United States Patent [19]

Wakasugi et al.

[11] Patent Number: 5,274,131

[45] Date of Patent: Dec. 28, 1993

[54] 2-CHLOROPIONALDEHYDE TRIMER AND PRODUCTION PROCESS THEREOF

[75] Inventors: Takashi Wakasugi; Tadashi Miyakawa; Naka Tonouchi; Takashi Yamauchi; Makoto Ishizuka, all of Fukushima, Japan

[73] Assignee: Kureha Chemical Industry Co., Ltd., Tokyo, Japan

[21] Appl. No.: 781,101

[22] Filed: Oct. 22, 1991

[30] Foreign Application Priority Data

Nov. 8, 1990 [JP] Japan .................. 2-303097

[51] Int. Cl.$^5$ .......................................... C07D 323/06
[52] U.S. Cl. ................................................. 549/368
[58] Field of Search ........................................ 549/368

[56] References Cited

U.S. PATENT DOCUMENTS 3,560,526  2/1971  Boudakian et al. ............... 544/368

FOREIGN PATENT DOCUMENTS 665062   1/1963   Canada ................................ 549/368
0368613  5/1990   European Pat. Off. .
2912767  10/1980  Fed. Rep. of Germany ...... 549/368
0186976  10/1984  Japan .................................. 549/368
1456754  11/1976  United Kingdom .

OTHER PUBLICATIONS

Chemical Abstracts vol. 93, #167080h, Barbulescu, 1980, "Aspects on nuclear magnetic resonance of 2-methyl-2(methylthio) propanal-O(methylcarbonyl)oxime and some intermediates."

Primary Examiner—C. Warren Ivy
Assistant Examiner—Raymond Covington
Attorney, Agent, or Firm—Burgess, Ryan & Wayne

[57] ABSTRACT

A novel compound, a 2-chloropropionaldehyde trimer and a process of producing a 2-chloropropionaldehyde trimer by adding concentrated sulfuric acid to an organic solvent containing 2-chloropropionaldehyde and stirring the mixture at a temperature of from −5° C. to 15° C. to carry out the reaction.

5 Claims, No Drawings

2-CHLOROPROPIONALDEHYDE TRIMER AND PRODUCTION PROCESS THEREOF

FIELD OF THE INVENTION

The present invention relates to a novel compound, 2-chloropropionaldehyde trimer and the production process thereof.

BACKGROUND OF THE INVENTION

2-Chloropropionaldehyde (hereinafter, is referred to as CPA) is a useful compound as a raw material for the organic synthesis of medicaments, agricultural chemicals, etc. However, since the compound is a very unstable compound, it can not be stably stored for a long period of time. Accordingly, in the case of using the compound, it must be prepared each time just prior to use and immediately supplied for a reaction, and hence the use of the compound is very troublesome.

SUMMARY OF THE INVENTION

An object of this invention is, therefore, to provide a novel compound, CPA trimer which can be stably stored and can be easily converted into CPA at use.

Other object of this invention is to provide a production process of the foregoing novel CPA trimer.

That is, according to the present invention, there is provided a 2-chloropropionaldehyde (CPA) trimer shown by the following formula;

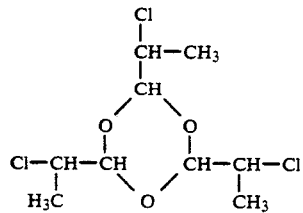

Furthermore, according to another embodiment of the present invention, there is provided a process of producing the CPA trimer shown by the foregoing formula, which comprises adding concentrated sulfuric acid to an organic solvent containing CPA and stirring the mixture at a temperature of from $-5°$ C. to $15°$ C. to carry out the reaction.

DETAILED DESCRIPTION OF THE INVENTION

The CPA trimer of the present invention is a white crystalline novel compound shown by the foregoing formula and the physical property values thereof are as follows; (the details are described in Example 1)

$^1$H NMR (60 MHz, CDCl$_3$); 4.9 ppm (1H, d, —CHO); 4.0 ppm (1H, m, —CH—); 1.5 ppm (3H, d, —CH$_3$).

Molecular weight (Mass): 276
IR: 1084 cm$^{-1}$ (C—O stretching)
Melting point: 55.1° C.

The CPA trimer is produced by adding concentrated sulfuric acid to an organic solvent containing CPA and stirring the mixture at a temperature of from $-5°$ C. to $15°$ C. to carry out the reaction.

As an organic solvent containing CPA, a solution obtained by distilling a chlorinated reaction mixture containing CPA obtained by chlorinating propionaldehyde at a temperature lower than the normal-pressure boiling point of CPA and taking out CPA distilled as a mixture thereof with an organic solvent can be used. To the solution is added sulfuric acid and the reaction is carried out by stirring the mixture at a temperature of from $-5°$ C. to $15°$ C. to provide the CPA trimer. The reaction mixture containing the CPA trimer obtained may be washed with water, concentrated, and then cooled to deposit the CPA trimer, which may be separated.

The chlorination reaction of propionaldehyde is carried by blowing a chlorine gas into propionaldehyde in an amount of from 0.7 to 0.8 mol per mol of propionaldehyde while maintaining the reaction temperature of from 0° C. to 20° C., and preferably from 2° C. to 10° C., whereby a chlorination reaction mixture containing at least 60% CPA can be obtained.

If the reaction temperature for the chlorination is lower than 0° C., the reaction rate is slow, which is unsuitable for practical purpose. On the other hand, if the reaction temperature is higher than 20° C., undesirable polychlorination products and high boiling materials are liable to form.

The chlorination reaction mixture obtained as described above is distilled to recover CPA and it is important that the distillation temperature in this case is lower than the normal pressure boiling point (86° C.) of CPA. If the reaction mixture is distilled at the normal pressure boiling temperature, high boiling materials are formed, whereby the amount of the distillate is reduced and the concentration of CPA in the distillate is undesirably reduced. Furthermore, when the distillate is subjected to a trimerization reaction, the yield and the purity of the CPA trimer obtained are undesirably low.

Also, since CPA is very unstable and undergoes change in a short period of time, CPA distilled by the foregoing distillation is recovered as a mixture with an organic solvent. Practically, the chlorination reaction mixture is distilled under reduced pressure, an organic solvent dissolving CPA is previously placed in a receiving vessel, and the CPA distilled is immediately recovered as a mixture with the organic solvent in the vessel.

The amount of the organic solvent being placed in the receiving vessel is such that the concentration of CPA is not over 80% by weight, and preferably not over 70% by weight. If the concentration of CPA in the mixture is higher, CPA is liable to change into a high boiling material and hence can not be stably stored. There may be some difference depending upon the organic solvent being used, thus when the concentration of CPA is not higher than 70% by weight, CPA can almost stably exist if the time is short.

In other method, an azeotropic solvent having a boiling point lower than that of CPA, such as benzene, carbon tetrachloride, etc., is added to the chlorination reaction mixture and CPA can be azeotropically distilled. In this case, it is preferable that the azeotropic solvent is gradually added when the chlorinated mixture being distilled is heated to a temperature of about 10° C. lower than the boiling point of the azeotropic solvent.

It is preferred that the organic solvent being used in the distillation does not, as a matter of course, react with CPA and does not readily react with sulfuric acid being used in the subsequent trimerization reaction. An organic solvent having a low boiling point is more preferably used. Examples of the preferred organic solvent are aromatic hydrocarbons such as benzene, etc., aliphatic hydrocarbons such as hexane, etc., alicyclic hydrocarbons such as cyclohexane, etc., and carbon tetrachloride.

CPA thus obtained as a mixture with the organic solvent is then subjected to a trimerization reaction and in this case, it is desirable that the concentration of CPA in the mixture is from 5 to 70% by weight, and preferably from 10 to 60% by weight. When concentrated sulfuric acid is added to the mixture and the reaction is carried out by stirring the mixture at a temperature of from $-5°$ C. to 15° C., and preferably from 0° C. to 10° C., a CPA trimer is formed. At the reaction, the amount of concentrated sulfuric acid being added as a catalyst is from 3 to 30% by weight, and preferably from 5 to 28% weight to the foregoing mixture. If the amount of concentrated sulfuric acid is less than 3% by weight, the trimerization reaction of CPA does not proceed sufficiently, while if the amount thereof is larger than 30% by weight, a large amount of high boiling materials are by-produced and the yield of the CPA trimer is reduced.

By reacting as described above, the trimerization of CPA is carried out and the CPA trimer formed exists as a solution in the organic solvent. If necessary, the sulfuric acid component is removed from the reaction mixture, the organic layer formed is washed with water or preferably washed with an aqueous sodium hydroxide solution and water, and after drying it with a drying agent such as magnesium sulfate, etc., the organic layer is concentrated and cooled to deposit and separate a CPA trimer. Thus, the CPA trimer having a purity of at least 95% is obtained. Furthermore, when the product is purified by recrystallizing from a solvent such as hexane, etc., the CPA trimer can be obtained as the crystals thereof having a purity of at least 99%.

The CPA trimer thus obtained can be stably stored for a long period of time at normal temperature. The CPA trimer can be supplied to a reaction with other compound as it is and also when the CPA trimer is heated to a temperature of from 120° C. to 130° C. at normal pressure in the existence of an acid catalyst such as p-toluenesulfonic acid, etc., pure CPA can be formed.

Accordingly, by depolymerizing the CPA trimer of this invention, high-pure CPA can be obtained. Also, the reaction of using CPA as a raw material can be carried out independently from the production of unstable CPA, whereby the utilization of CPA as a synthetic raw material can be remarkably facilitated.

Then, the invention is more practically explained by referring to the following examples and comparison examples but the invention is not limited to these examples.

EXAMPLE 1

In a two liter three neck distillation flask equipped with a stirrer, a refux condenser and a thermometer was placed 800 g of propionaldehyde and it was kept at 5° C. Into the propionaldehyde was introduced a chlorine gas at 100 ml/min. to initiate the chlorination reaction. Thereafter, while the reaction temperature was kept at 5° C.±1° C., 10.5 mol of a chlorine gas was introduced therein at a rate of from 200 ml/min. to 800 ml/min. Hydrogen chloride formed was introduced into an aqueous solution of sodium hydroxide.

Then, while 1050 g of benzene was added to 1180 g of the chlorination reaction mixture at a rate of about 3.0 g/min. from a liquid temperature of 70° C., an azeotropic distillation was carried out and 1830 g of a distillate was obtained at a distilled temperature of from 71° C. to 81° C.

As the result of analyzing the composition of the distillate by gas chromatography, it was confirmed that the distillate was composed of 38.8% by weight CPA, 57.3% by weight benzene and a slight amount of high boiling materials. The distilled amount was 66% of the raw material chlorinated mixture and CPA obtained was 710 g.

The synthesis of the trimer using the distillate was carried out by using a two liter three neck distillation flask equipped with a stirrer and a thermometer. After cooling 1450 g of the distillate having the foregoing composition to 2° C., 70 ml (8.9% by weight to the distillate being charged for the reaction) of concentrated sulfuric acid of 96% was gradually added thereto over a period of one hour and while keeping at a temperature of lower than 5° C., the mixture was stirred for 2 hours to perform the trimerization reaction.

After the reaction was over, the reaction mixture obtained was allowed to stand, the sulfuric acid layer formed was removed, and the organic layer formed was collected and washed with water and an aqueous 10% sodium hydroxide solution. Then, after removing the solvent from the organic solution obtained under reduced pressure (20 mm Hg), the residue was allowed to stand at room temperature to provide 342 g of white crystals of the CPA trimer having a purity of 99.2%. The synthesis yield of the CPA trimer obtained was 60.3% to CPA in the distillate used for the trimerization reaction. The crystals formed were recovered by filtration and recrystallized using 300 ml of hexane to provide 312 g of white crystals of the CPA trimer having a purity of 99.8%.

By NMR, GC-MS, IR and the elemental analysis, the structure was confirmed to be the CPA trimer shown by the following formula, wherein a 6-membered ring was formed by 3 molecules of CPA.

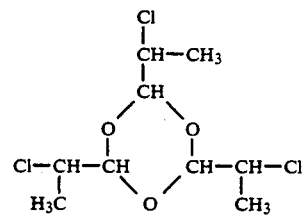

Then, the analysis values are shown below.
$^1$H NMR (60 MHz, CDCl$_3$); 4.9 ppm (1H, d, —CHO); 4.0 ppm (1H, m, —CH—); 1.5 ppm (3H, d, —CH$_3$).
Molecular weight (Mass): 276
IR: 1084 cm$^{-1}$ (C—O stretching)
Elemental Analysis: (weight %)

|  | C | H | O |
| --- | --- | --- | --- |
| Found: | 38.9% | 5.4% | 17.1% |
| Calculated: | 38.94% | 5.45% | 17.29% |

Melting Point: 55.1° C.

EXAMPLE 2

In place of the azeotropic distillation of the chlorination reaction mixture obtained by the chlorination condition shown in Example 1, a distillation under reduced pressure was carried out.

That is, 250 g of the chlorination reaction mixture was charged in a 300 ml three neck distillation flask and the distillation was carried out at 300 mmHg. The distillate formed was directly dissolved in 150 g of hexane previously placed in a 500 ml vessel to provide 328 g of a mixture with hexane.

As the result of the analysis of the composition of the mixture by gas chromatography, it was confirmed that the mixture was composed of 49.3% by weight CPA, 45.2% by weight hexane and a slight amount of high boiling materials. The distilled amount was 71% of the raw material chlorinated mixture and the amount of CPA was 161.7 g.

The synthesis of a CPA trimer using the mixture was carried out by using a 500 ml three neck distillation flask equipped with a stirrer and a thermometer. That is, 300 g of the mixture having the foregoing composition was cooled to 5° C. in the flask and 15 ml (9.2% by weight to the mixture charged for the reaction) of concentrated sulfuric acid of 96% was gradually added to the mixture with stirring over a period of one hour and while keeping the temperature below 3° C., the mixture was stirred for 2.5 hours to carry out the trimerization reaction.

After the reaction was over, the reaction mixture obtained was allowed to stand, a sulfuric acid layer formed was removed, and an organic layer formed was washed with water and an aqueous 10% sodium hydroxide solution. Then, after distilling off the solvent from the solution formed under reduced pressure (20 mmHg), the residue was allowed to stand at room temperature to provide 96.2 g of white crystals of a CPA trimer having a purity of 99.5%. The synthesis yield of the CPA trimer was 64.7% to CPA in the mixture used for the trimerization reaction.

COMPARISON EXAMPLE

In place of the azeotropic distillation of the chlorination reaction mixture obtained under the chlorination condition shown in Example 1 and the distillation under reduced pressure shown in Example 2, a normal pressure distillation was carried out.

That is, 125 g of the chlorination reaction mixture was charged in a 200 ml three neck distillation flask and by carrying out a distillation at normal pressure, 52.6 g of a distillate was obtained.

As the result of carrying out the analysis of the composition of the distillate by gas chromatography, it was confirmed that the distillate was composed of 56.2% by weight CPA and a large amount of high boiling materials. The distilled amount was 42% of the raw material chlorination mixture and the amount of CPA obtained was 29.6 g.

The synthesis of a CPA trimer using the distillate was carried out by using a 200 ml three neck distillation flask equipped with a stirrer and a thermometer. Thus, 50.2 g of the distillate having the foregoing composition was placed in the flask, 100 g of hexane was immediately added to the distillate, and after cooling the mixture to 3° C., 8 ml (9.8% by weight to the mixture charged for the reaction) of concentrated sulfuric acid of 96% was gradually added to the mixture with stirring over a period of one hour. Then, while keeping the mixture at a temperature below 2° C., the mixture was stirred for 2 hours to carry out the trimerization reaction.

After the reaction was over, the reaction mixture was allowed to stand, a sulfuric acid layer formed was removed and an organic layer formed was washed with water and an aqueous 10% sodium hydroxide solution. Then, after distilling off the solvent from the solution obtained under reduced pressure (20 mmHg), the residue was allowed to stand at room temperature to provide 12.7 g of white crystals of a CPA trimer having a purity of 92.5%. The synthesis yield of the CPA trimer was 41.6% to CPA in the mixture used for the trimerization reaction.

What is claimed is:

1. A 2-chloropropionaldehyde trimer shown by the following formula;

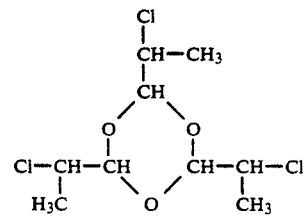

2. A process for producing 2-chloropropionaldehyde trimer which comprises the following successive steps:
   a) chlorination of propionaldehyde to give chlorinated reaction mixture containing 2-chloropropionaldehyde,
   b) distillation of the chlorinated reaction mixture at a temperature lower than the boiling point of 2-chloropropionaldehyde at normal pressure to give a mixture of 2-chloropropionaldehyde with an organic solvent, and
   c) addition of concentrated sulfuric acid to the mixture containing 2-chloropropionaldehyde to cause a reaction at a temperature of −5° C. to 15° C. and form the 2-chloropropionaldehyde trimer.

3. The process according to claim 2, wherein an azeotropic distillation is carried out by adding an organic solvent.

4. The process according to claim 2, wherein the distillation is carried out under reduced pressure and the distillate is received in a receiver containing an organic solvent.

5. A process for producing 2-chloropropionaldehyde trimer which comprises the following successive steps:
   a) chlorination of propionaldehyde to give a chlorinated reaction mixture containing 2-chloropropionaldehyde,
   b) distillation of the chlorinated reaction mixture at a temperature lower than the boiling point of 2-chloropropionaldehyde at reduced pressure to give a mixture of 2-chloropropionaldehyde with an organic solvent, wherein the concentration of said 2-chloropropionaldehyde in said solvent does not exceed 80% by weight, and
   c) addition of concentrated sulfuric acid to the mixture containing 2-chloropropionaldehyde in an amount of from 3 to 30% by weight to cause a reaction at a temperature of −5° C. to 15° C. and form the 2-chloropropionaldehyde trimer.

* * * * *